United States Patent [19]

Numa et al.

[11] Patent Number: 4,518,527
[45] Date of Patent: May 21, 1985

[54] POLYPEPTIDES RELATED TO THE PRE-ACETYLCHOLINE RECEPTOR-α OF THE ELECTRIC ORGAN OF *TORPEDO CALIFORNICA*

[75] Inventors: Shosaku Numa, Kyoto; Noboru Yanaihara, Shizuoka, both of Japan

[73] Assignee: Mitsubishi Chemical Industries Limited, Tokyo, Japan

[21] Appl. No.: 523,787

[22] Filed: Aug. 16, 1983

[51] Int. Cl.³ .......................................... C07C 103/52
[52] U.S. Cl. ............................................. 260/112.5 R
[58] Field of Search ................................ 260/112.5 R

[56] References Cited

PUBLICATIONS

Proc. Nat'l Acad. Sci., vol. 75, (1978), 769–773.
Biochemistry, vol. 18, (1979), 4470–4480.
Lindstrom and Lennon, "Experimental Autoimmune Myasthenia Gravis and Myasthenia Gravis: Biochemical and Immunochemical Aspects", *Annals New York Academy of Sciences*, pp. 254–274.
Almon et al., "Serum Globulin in Myasthenia Gravis: Inhibition of α-Bungarotoxin Binding to Acetylcholine Receptors", *Science*, vol. 186, Oct. 1974, pp. 55–57.
Patrick and Lindstrom, "Autoimmune Response to Acetylcholine Receptor", *Science*, vol. 180, May 1973, pp. 871–872.
Fambrough et al., "Neuromuscular Junction in Myasthenia Gravis: Decreased Acetylcholine Receptors", *Science*, vol. 182, Oct. 1973, pp. 293–295.

*Primary Examiner*—Delbert R. Phillips
*Attorney, Agent, or Firm*—Oblon, Fisher, Spivak, McClelland & Maier

[57] ABSTRACT

Polypeptides having partial or complete amino acid sequences related to the pre-acetylcholine receptor-α of the electric organ *Torpedo californica* are disclosed. These polypeptides having AChR antigenic properties are useful for the production and purification of antibodies to the acetylcholine receptor (AChR) as well as for the diagnosis of myastenia gravis (MG).

15 Claims, No Drawings

POLYPEPTIDES RELATED TO THE PRE-ACETYLCHOLINE RECEPTOR-α OF THE ELECTRIC ORGAN OF *TORPEDO CALIFORNICA*

BACKGROUND OF THE INVENTION

1. Field of the Invention

The present invention relates to polypeptides having amino acid sequences related to the preacetylcholine receptor-α of the electric organ of *Torpedo californica*. These polypeptide sequences are useful for the production and purification of antibodies to the receptor acetylcholine receptor, as well as, for the diagnosis of myasthenia gravis (MG).

2. Description of the Prior Art

Myastenia gravis (MG) is a neuromuscular disorder manifested by muscular weakness and fatigability. Recent studies suggest physiological and immunological involvement of the muscle acetylcholine receptor (AChR) in MG (See Patrick and Lindstrom, Science 180:871 (1973), and Fambrough et al, Science 182:294 (1973)).

Almon et al, Science 186:55 (1974), demonstrated the presence in some MG patients of circulating globulins with affinity for the muscle AChR.

Lindstrom et al, Annals of the New York Academy of Science: 254–274, (1976), confirmed the existence of antibodies to AChR in MG patients, as well as in an animal model for this disease. In addition, this reference describes an antibody assay for the detection of anti AChR proteins in the blood of MG patients using human AChR protein radiolabeled with $^{125}$I-Toxin.

One particularly useful modification of interest to those of skill in this art, would be to develop peptides having AChR-like activity. These polypeptides having AChR antigenic activity could be useful in the production of antibodies to the AChR protein and affinity purification thereof, as well as in the measurement of antibody levels in the blood of patients suspected of suffering from MG. These polypeptides, having high specific affinity for anti AChR protein molecules, may also be useful in the treatment of MG in mammals, including humans.

A need therefore continues to exist for polypeptides useful for the production of anti AChR antibodies, and for the affinity purification, thereof especially for the diagnosis of MG in humans.

SUMMARY OF THE INVENTION

It is an object of this invention to provide polypeptides containing amino acid sequences related to the pre-acetylcholine receptor-α of the electric organ of *Torpedo californica.* Another object is to provide polypeptides having high specific affinity for anti AChR protein molecules.

A further object is to provide polypeptides useful in the affinity purification of anti AChR antibody molecules from mammals, including humans.

Still another object of this invention is to provide polypeptides useful for the measurement of anti AChR protein levels in the blood of patients suspected of suffering from MG.

These and other objects of this invention, as will hereinafter become more readily apparent, have been attained by providing:

a peptide comprising the following amino acid sequences:

(a) 1-Ser-Glu-His-Glu-Thr-Arg
(b) 74-Gly-Ile-Lys-Lys-Ile-Arg
(c) 79-Arg-Leu-Pro-Ser-Asp-Asp
(d) 94-Asn-Asn-Ala-Asp-Gly-Asp
(e) 161-Glu-Ser-Asp-Arg-Pro-Asp
(f) 179-Lys-Asp-Tyr-Arg-Gly
(g) 237-Thr-Asp-Ser-Gly-Glu-Lys
(h) 330-Lys-Arg-Ala-Ser-Lys-Glu-Lys-Gln-Glu-Asn-Lys
(i) 368-Lys-Asn-Pro-Asp-Val-Lys
(j) 387-Lys-Ser-Asp-Glu-Glu-Ser
(k) 71-Asp-Tyr-Gly-Gly-Ile-Lys
(l) 195-Asp-Thr-Pro-Tyr-Leu-Asp
(m) 301-Arg-Ser-Pro-Ser-Thr-His, or
(n) pharmaceutically acceptable acid-addition salts thereof.

Also provided herein are polypeptides comprising at least one of the hereinbefore-described amino acid sequences or their acid-addition salts and having the formula:

X—A—Y wherein

A is the radical of the already described amino acid sequence, wherein the amino acids are in the L-configuration;

X is lower alkyl, lower acyl, a carrier protein, or a peptide wherein the amino acid residue in the carrier protein and the peptide may be in the L- or D-configuration;

Y is amino, lower alkylamino, dilower alkylamino, lower alkoxy, a carrier protein or a peptide wherein the amino acid residue in the carrier protein and the peptide may be in L- or D-configuration; and X and Y taken together may form a ring containing a disulfide, ether or ester bond.

DESCRIPTION OF THE PREFERRED EMBODIMENTS

The present invention arose from the recent determination by one of the present inventors of the sequence of pre-acetylcholine receptor-α from the electric organ of *Torpedo californica.* This amino acid sequence is shown in FIG. 1 and was determined from a complementary deoxyribonucleotide sequence (cDNA) to messanger ribonucleic acid (mRMA) extracted from the electric organ of *Torpedo californica.*

What the present inventors have done, is to locate antigenic determinants in the complete amino acid sequence of this protein. For this, a method known in the prior art was used (see, Hopp and Wood, Proc. Nat. Acad. Sci. (USA) 78:3824–3828 (1981), and Chou and Fasman, G.D. Adv. Enzym. 47:45–148 (1978)). This method can be used to locate antigenic determinants in proteins, by analyzing amino acid sequences for points of greater local hydrophillicity and β-sheet structure.

FIG. 1: Amino acid sequence of the pre-acetylcholinereceptor-α of Torpedo californica.

−20

Met Ile Leu Cys Ser Tyr Trp His Val Gly Leu Val

FIG. 1: Amino acid sequence of the pre-acetylcholinereceptor-α of Torpedo californica.

| | −1  1 | 10 |
|---|---|---|
| Leu Leu Leu Phe Ser Cys Cys Gly Leu Val Leu | Gly Ser Glu His Glu Thr Arg Leu Val Ala | Asn Leu Leu Glu Asn Tyr Asn Lys Val |
| 20 | 30 | 40 |
| Ile Arg Pro Val Glu His His Thr His Phe Val | Asp Ile Thr Val Gly Leu Gln Leu Ile Gln | Leu Ile Ser Val Asp Glu Val Asn Gln |
| 50 | 50 | 70 |
| Ile Val Glu Thr Asn Val Arg Leu Arg Gln Gln | Trp Ile Asp Val Arg Leu Arg Trp Asn Pro | Ala Asp Tyr Gly Gly Ile Lys Lys Ile |
| 30 | 90 | 100 |
| Arg Leu Pro Ser Asp Asp Val Trp Leu Pro Asp | Leu Val Leu Tyr Asn Asn Ala Asp Gly Asp | Phe Ala Ile Val His Met Thr Lys Leu |
| 110 | 120 | 130 |
| Leu Leu Asp Tyr Thr Gly Lys Ile Met Trp Thr | Pro Pro Ala Ile Phe Lys Ser Tyr Cys Glu | Ile Ile Val Thr His Pha Pro Phe Asp |
| 140 | 150 | 160 |
| Gln Gln Asn Cys Thr Met Lys Leu Gly Ile Trp | Thr Tyr Asp Gly Thr Lys Val Ser Ile Ser | Pro Glu Sar Asa Arg Pro Asp Leu Ser |
| 170 | 120 | 150 |
| Thr Phe Met Glu Ser Gly Glu Trp Val Met Lys | Asp Tyr Arg Gly Trp Lys His Trp Val Tyr | Tyr Thr Cys Cys Pro Asp Thr Pro Tyr |
| 200 | 210 | 220 |
| Leu Asp Ile Thr Tyr His Phe Ile Met Gln Arg | Ile Pro Leu Tyr Phe Val Val Asn Val Ile | Ile Pro Cys Leu Leu Phe Ser Phe Leu |
| 230 | 240 | 250 |
| Thr Gly Leu Val Phe Tyr Leu Pro Thr Asp Ser | Gly Glu Lys Met Thr Leu Ser Ile Ser Val | Leu Leu Ser Leu Thr Val Phe Leu Leu |
| 260 | 270 | 280 |
| Val Ile Val Glu Leu Ile Pro Ser Thr Ser Ser | Ala Val Pro Leu Ile Gly Lys Tyr Met Leu | Phe Thr Met Ile Phe Val Ile Ser Ser |
| 290 | 300 | 310 |
| Ile Ile Ile Thr Val Val Val Ile Asn Thr His | His Arg Ser Pro Ser Thr His Thr Met Pro | Gln Trp Val Arg Lys Ile Phe Ile Asp |
| 320 | 330 | 340 |
| Thr Ile Pro Asn Val Met Phe Phe Ser Thr Met | Lys Arg Ala Ser Lys Glu Lys Gln Glu Asn | Lys Ile Phe Ala Asp Asp Ile Asp Ile |
| 350 | 360 | 370 |
| Ser Asp Ile Ser Gly Lys Gln Val Thr Gly Glu | Val Ile Phe Gln Thr Pro Leu Ile Lys Asn | Pro Asp Val Lys Ser Ala Ile Glu Gly |
| 380 | 390 | 400 |
| Val Lys Tyr Ile Ala Glu His Met Lys Ser Asp | Glu Glu Ser Ser Asn Ala Ala Glu Glu Trp | Lys Tyr Val Ala Met Val Ile Asp His |
| 410 | 420 | 430 |
| Ile Leu Leu Cys Val Phe Met Leu Ile Cys Ile | Ile Gly Thr Val Ser Val Phe Ala Gly Arg | Leu Ile Glu Leu Ser Gln Glu Gly |

The polypeptides of the present invention are those comprising at least one of the following amino acid sequences:

(a) 1-Ser-Glu-His-Glu-Thr-Arg,
(b) 74-Gly-Ile-Lys-Lys-Ile-Arg,
(c) 79-Arg-Leu-Pro-Ser-Asp-Asp,
(d) 94-Asn-Asn-Ala-Asp-Gly-Asp,
(e) 161-Glu-Ser-Asp-Arg-Pro-Asp,
(f) 179-Lys-Asp-Tyr-Arg-Gly,
(g) 237-Thr-Asp-Ser-Gly-Glu-Lys,
(h) 330-Lys-Arg-Ala-Ser-Lys-Glu-Lys-Gln-Glu-Asn-Lys,
(i) 368-Lys-Asn-Pro-Asp-Val-Lys,
(j) 387-Lys-Ser-Asp-Glu-Glu-Ser,
(k) 71-Asp-Tyr-Gly-Gly-Ile-Lys,
(l) 195-Asp-Thr-Pro-Tyr-Leu-Asp,
(m) 301-Arg-Ser-Pro-Ser-Thr-His; or
(n) pharmaceutically-acceptable acid-addition salts thereof.

The number before the amino acid sequence indicates the position of the first amino acid in the amino acid sequence of pre-acetylcholine receptor-α.

Some of the polypeptides of the present invention comprising the above-described amino acid sequences as their partial structure, are represented by the following formula:

wherein
A is the residue of the amino acid sequence described above, wherein the amino acid residues are in the L-configuration;
X is lower alkyl of $C_1-C_{10}$, lower acyl of $C_1-C_{10}$, a carrier protein or a peptide, wherein the amino acid residues in the carrier protein and the peptide may be in L- or D-configuration;
Y is amino, lower alkylamino of $C_1-C_{10}$, dilower alkylamino of $C_1-C_{10}$, lower alkoxy of $C_1-C_{10}$, a carrier protein or a peptide, wherein the amino acid residues in the carrier protein and the peptide may be in L- or D-configuration; and
X and Y taken together may form a ring containing a disulfide, ether or ester bond.

Examples of the carrier proteins which may be X and/or Y include human and bovine albumin, collagen, hemocyanin, fibrinogen, human erythrocyte, synthetic poly (amino acid) such as poly (glutamic acid), polylysine and the like. However, any protein can be used after attachment to the polypeptides of the present invention.

Additional peptides which may be X and/or Y may either have the partial amino acid sequence adjacent to A in the amino acid sequence of pre-acetylcholine receptor-α or may have any amino acid sequence different from that of pre-acetylcholine receptor-α. X and Y may, of course, contain one or more of the above-described amino acid sequences indicated by A in the formula. A typical number of amino acids which are included in the additional peptide is 1 to 10, and preferably 5 to 10.

Non-toxic pharmaceutically acceptable acid addition salts of the polypeptides can be produced by methods well known in the art. Some of the preferred salts are those obtained from hydrochloric, hydrobromic, sulfuric, phosphoric, maleic, acetic, citric, benzoic, succinic, malonic or ascorbic acid.

The polypeptides of this invention can be prepared by solid phase methodology, following techniques generally known in the art for constituting an amino acid sequence from an initial resin supported amino acid (see, Merrifield, J.A.C.C., 85, 2149 (1963) as an illustration for the general technique.

The preparation of one of the preferred polypeptides is exemplified in the example. The preparation of other polypeptides can be attained using the method and procedure described in the example, or obvious modifications thereof. A desired polypeptide can be prepared using the described techniques by substituting an appropriate amino acid or protected amino acid for a particular amino acid or protected amino acid described in the example.

In general, the preparation of the polypeptides of this invention can be accomplished as follows. A protected amino acid is attached to a chloromethylated polystyrene resin or benzhydryl amine polystyrene resin and the α-amino protecting group is removed with trifluoroacetic acid in methylene chloride. The removal of the protecting group is conducted at a temperature between about 0° C. and room temperature (40° C.).

Other methods can be used for removal of amino protecting groups as described in S.E. Lubke, "The Peptides", 1, 72–75 (Academic Press, 1965). After removal of the amino protecting group, the subsequent protected amino acids are coupled individually to the resin-supported sequence.

Alternatively, small peptide fragments may be prepared by the solution method and introduced into the solid phase reactor in the desired order. Each protected amino acid sequence is introduced into the solid phase reactor in excess. The coupling can be carried out in dimethylformamide, methylene chloride or a mixture of the two solvents. Different coupling reagents can be used, the preferred coupling reagent being diisopropylcarbodiimide.

After the desired amino acid sequence has been synthesized, the polypeptide is removed from the resin support by conventional methods known in the art of synthesizing polypeptides.

In the solution method, the preparation of the polypeptides of this invention involves coupling of an amino acid having a free amino group and an amino acid having a free carboxyl group and a protected amino group in the presence of a condensing agent, e.g., a carbodiimide such as 1,3-dicyclohexylcarbodiimide. After completion of the reaction, the excess carbodiimide is converted to the corresponding urea by acidification, the pH is adjusted to near neutrality and the urea is removed by filtration. The products may be recovered from the solution by acidification or extraction.

Additionally, in order to realize the coupling, it is essential, first, that all reactive functional groups not participating directly in the reaction be inactivated by appropriate blockage, and secondly, that the carboxy or amino function which is to be coupled, be activated to permit the coupling to proceed.

Preferably protecting groups are benzyloxycarbonyl (Z), tert-butyloxycarbonyl (t-Boc) for protecting α-amino groups; benzyl (Bzl), for protecting a side chain hydroxy group; and tosyl, for protecting a side chain guanidine. In order to render the carboxy function active for the coupling reaction, the carboxy function can be converted to an acid halide, acid azide, activated ester (e.g., p-nitrophenyl ester) or mixed carbonic anhydride. These acylating agents need not be isolated, since it is frequently more convenient and practical to use them in the same solution in which they were prepared.

The conversion of the amino acid or its N-substituted derivative to a mixed carbonic anhydride is effected by dissolving the amino acid or its N-substituted derivative in a ketone solvent containing a tri-(lower)alkylamine and treating the solution with an anhydride forming reagent, e.g., a lower alkyl chloroformate or an aryl chloroformate at a temperature of from 0° to −20° C. The peptides are obtained by reacting the mixed anhydride with an amino acid at a temperature of about −50° to +10° C. Recovery of the product can be effected by precipitation (after acidification of the reaction mixture) or by extraction with an organic solvent, e.g., ethyl acetate, methyl isobutyl ketone or the like, from the acidified reaction mixture.

The N-blocking groups are cleaved in the presence of an acid, e.g., trifluoroacetic acid, p-toluenesulfonic acid or the like, to form the respective acid-addition salt products. The cleavage can also be accomplished by hydrogenation in the presence of a catalyst, e.g., palladium, Raney nickel, platinum or rhodium. In general, hydrogenation is effected in a suitable solvent, e.g., water, methanol, tetrahydrofuran, acetone, acetic acid or the like, at a temperature in the range of 0° to 60° C., and preferably at room temperature. The hydrogen pressure is not critical, and can be either below, above or about atmospheric pressure.

The particular methods of coupling, blocking and cleavage employed in preparing the compounds of this invention are, each and all, well recognized in the art. The conditions under which a particular coupling, blocking or cleavage reaction would be carried out will be apparent to those skilled in the art.

Coupling of the synthetic polypeptides to the carrier protein or the additional peptide can be accomplished by conventional methods, well known in the art.

The above-described general methods of coupling can be applied to coupling of the synthetic polypeptide (A) of this invention to the carrier protein or the additional polypeptide (X and Y).

The peptides of this invention have antigenic properties, which are made evident when injected to mammals by eliciting the production of antibody molecules directed against the peptides. For the purpose of enhancing antigenic activity, cyclic disulfides, esters and ethers can be formed between X and Y. Cyclic disulfides can be formed between cysteines contained in X and Y. Cyclic esters can be formed between hydroxyl group and carboxyl group contained X and Y. The reaction conditions for the ring formation are also well known in the art.

The antigenic polypeptides of this invention are useful in the affinity purification of antiAChR antibody proteins or other related polypeptides. Knowledge of the structure of these macromolecules is paramount in the elucidation of the possible mechanisms of MG in humans, since it is believed that the interaction of endogenously produced AChR antibodies are involved in the inactivation of the AChR protein in patients affected with this disease. In addition, modified antiAChR antibodies can be useful for interfering or inhibiting the antigenically specific interaction of the AChR protein molecule and the antiAChR antibody.

In addition, the present polypeptides are also useful in the detection of patients suffering from MG and possibly other humans who may have elevated antibody titers but who do not show the full spectrum of MG symptomatology. Assays relying on the utilization of the highly specific antibodyantigen interaction can be utilized for screening of a particular population at risk.

For use in the affinity purification of anti AChR antibody or related molecules, these polypeptides can be coupled, e.g., with a CNBr-activated Sepharose substrate. The coupling methods are widely known in the art of preparing substrates for affinity purification.

The affinity purification of proteins is widely known and practiced in the field of protein purification. Specifically, the isolation of anti AChR protein molecules can be accomplished by contacting a pre-packed column containing the polypeptide-bound substrate with the protein-containing sample in a suitable buffer, such as PBS. Blood samples can be citrated prior to loading the column, although this step is seldom necessary. After sufficient washing, the retained protein may be eluted from the column with a suitable buffer, e.g., about 0.1 M glycine-HCl.

The peptides of this invention can, in addition, be absorbed on polyvinylpyrrolidone or carbon powder.

These peptides can be utilized for the detection of the antibodies in blood samples by any of the assay methods known in the art, e.g., radioimmunoassays (RIA), double antibody assays, and the like.

One such assay would be a solid-phase enzyme-linked immunosorbent assay for anti AChR antibodies using microtiter plates. An antigenic polypeptide of the present invention bound to the plate could be reacted with standards or samples containing anti AChR antibodies and the antibodies bound to the polypeptides molecules. Rabbit anti-human antibody will then be reacted to bind to the constant region of the human anti AChR antibody. If necessary to increase sensitivity, goat anti-rabbit immunoglobulin (IgG), or Staph protein A, can be added to bind to the constant region of the rabbit antibody. Or, further, either one of these proteins can be labelled with an enzyme, e.g. alkaline phosphatase which can be assayed colorimetrically, or by the utilization of radiolabelled substrate. The color development or cpm released will directly correlate to the amount of anti AChR antibody present in the clinical samples. For diagnostic purposes, some of the amino acids contained in X and Y can be those labelled with $^3H$, $^{13}C$, $^{14}C$ or $^{32}S$. It is also preferred that X contain tyrosine, hydroxyphenylpropionyl group, histidine and/or cysteine which can be labelled with $^{125}I$ or $^{131}I$.

Having now generally described this invention, the same will be understood by reference to a specific example, which is included herein for purposes of illustration only, and is not intended to be limiting, unless otherwise specified.

EXAMPLE

(1) Z-Glu(OBzl)-Ser-OH (MW 458.47) (I)

To a solution of Z-Glu(OBzl)OH (5.62 g, 15 m mole) (Hayakawa et al. Bull. Chem. Soc. Japan, 39: 391 (1966)) in tetrahydrofuran (20 ml), N-methylmorpholin (1.53 ml) and isobutyl chloroformate (1.98 ml) were added with stirring at $-15°$ C. To this mixture a solution of HOSu (N-hydroxy-succinimide) (3.45 g) in tetrahydrofuran (10 ml) was added with stirring at $-15°$ C. The mixture was stirred at $-15°$ C. for 30 min., and at $0°$ C. for 30 min. To this mixture a solution of H-Ser-OH (3.15 g, 30 mmole) in $H_2O$ (15 ml) containing triethylamine (4.2 ml) was added with stirring at $0°$ C. The mixture was stirred at $0°$ C. for 2 hr. and at room temperature for 15 hr. After removal of the organic solvent, the residue was extracted with three portions of ethyl acetate, which were washed successively with 1N citric acid and sat. NaCl solution, and dried over $Na_2SO_4$. After evaporating the residue was solidified by addition of ether. Reprecipitation from methanol-ether to yield (I) (5.29 g, 76.9%), $Rf^I$ 0.74 $Rf^{II}$ 0.70, mp $104°–105°$ C. $[\alpha]_D^{27} +5.7$ (C=1.12 in methanol).

Anal. Calcd. for $C_{23}H_{26}N_2O_8$: C, 60.26; H, 5.65; N, 6.11.Found: C, 60.33; H, 5.65; N, 5.95.

Solvent system: $Rf^I$, 1-BuOH-AcOH-$H_2O$ (4:1:5). $Rf^{II}$, 1-BuOH-pyridine-AcOH (30:20:6:24)

(2) Z-Glu(OBzl)-Glu-Ser-OH (MW 587.59) (II)

I (2.20 g, 4.80 mmole) was hydrogenated in methanol (50 ml) and $H_2O$ (20 ml) over Pd for 15 hr. After filtering and evaporating the solvents, the residue was solidified from ether. ($Rf_I$ 0.18, $Rf^{II}$ 0.26). To a solution of Z-Glu(OBzl)OH (2.67 g, 7.2 mmole) in N,N'-dimethylformamide (15 ml), N-methylmorpholin (0.73 ml) and isobutyl chloroformate (0.95 ml) were added with stirring at $-15°$ C. To this mixture a solution of HOSu (1.65 g) in N,N'-dimethylformamide (7 ml) was added with stirring at $-15°$ C. The mixture was stirred at $-15°$ C. for 30 min. and at $0°$ C. for 30 min. To this mixture a solution of the above deprotected dipeptide in N,N'-dimethylformamide (15 ml) and $H_2O$ (5 ml) containing triethylamine (1.34 ml) was added with stirring at $0°$ C. The mixture was stirred at $0°$ C. for 2 hr. and at room temperature for 15 hr. After removal of the solvents, the residue was dissolved in three portions of ethyl acetate, which were washed successively with 1N citric acid and a sat. NaCl solution, and dried over $Na_2SO_4$. After evaporating the residue was solidified by addition of ether, and reprecipitated from methanol-ether to yield (II). (2.20 g, 78.0%), $Rf^I$ 0.74, $Rf^{II}$ 0.69, mp $165°–167°$ C., $[\alpha]_D^{24} -13.8$ (C=1.03 methanol)

Anal. Calcd. for $C_{28}H_{33}N_3O_{11}$: C, 57.24; H, 5.66; N, 7.15. Found: C, 57.06; H, 5.51; N, 7.05.

(3) Z-Asp(OBzl)-Glu-Glu-Ser-OH (MW 702.679) (III)

Compound II (1.18 g, 2.0 mmole) was hydrogenated in methanol (40 ml) and $H_2O$ (10 ml) over Pd for 15 hr. After filtering and evaporating the solvent, the residue was solidified by addition of ether. $Rf^I$, 0.18, $Rf^{II}$, 0.24.

To a solution of Z-Asp(OBzl)OH (1.43 g, 4.0 mmole) (see Davey et al. J. Chem. Soc., 555 (1966)) in N,N'-dimethylformamide (15 ml), N-methylmorpholin (0.41 ml) and isobutyl chloroformate (0.53 ml) were added with stirring at $-15°$ C. To this mixture a solution of HOSu (0.69 g) in N,N'-dimethylformamide (7 ml) was added with stirring at $-15°$ C. The mixture was stirred at $-15°$ C. for 30 min. and at $0°$ C. for 30 min. To this mixture, a solution of the above deprotected tripeptide in N,N'-dimethylformamide (10 ml) and $H_2O$ (5 ml) containing triethylamine (0.84 ml) was added with stirring at $0°$ C. The mixture was stirred at $0°$ C. for 2 hr. and at room temperature for 15 hr. After removal of the solvent, the residue was solidified, by addition of 1N citric acid and washed with $H_2O$. Reprecipitation of the product was from methanol-ether to yield Compound III (1.14 g, 81.1%). $Rf^I$ 0.69, $Rf^{II}$ 0.60, $[\alpha]_D^{24} -21.6$ (C=1.05 in methanol)

(4) Z-Lys(Z)-Ser-OMe (MW 515.569) (IV)

To a solution of Z-Lys(Z)OSu (1.50 g, 2.93 mmole) (see Chladek et al. Collect. Czechr. Chem. Commun. 33: 4299 (1968)) in tetrahydrofuran (15 ml), a solution of H-Ser-OMe-HCl (0.46 g, 2.93 mmole) in N,N'-dimethylformamide (10 ml) containing triethylamine (0.41 ml) was added with stirring at $0°$ C. The mixture was stirred at $0°$ C. for 2 hr. and at room temperature for 15 hr. After removal of the solvent, the residue was dissolved in three portions of ethyl acetate, which were washed successively with 1N citric acid, sat. $NaHCO_3$ solution and sat. NaCl solution, and dried over $Na_2SO_4$. After evaporating, the residue was solidified by addition of ether and reprecipitated from methanol-ether to yield (IV) (1.19 g, 78.8%). $Rf^I$ 0.88, $Rf^{II}$ 0.86 mp $120°–121°$ C., $[\alpha]_D^{29} -7.8$ (C=1.03 methanol)

Anal. Calcd. for $C_{26}H_{33}N_3O_8$: C, 60.57; H, 6.45; N, 8.15. Found: C, 60.61; H, 6.42; N, 8.11.

(5) Z-Lys(Z)-Ser-$N_2H_3$ (MW 515.567) (V)

(IV) (1.05 g, 2.04 mmole) was dissolved in methanol (20 ml) and thereto hydrazine hydrate (0.99 ml) was added at 0° C. This mixture was allowed to stand at room temperature for 20 hr. The precipitate was filtered, washed with ether and reprecipitated from methanol-ether to yield (V) (1.01 g, 96.0%). $Rf^I$ 0.75, $Rf^{II}$ 0.79, mp 165°–166° C., $[\alpha]_D^{27}$ −7.8 (C=1.09 AcOH).

Anal. Calcd. for $C_{25}H_{33}N_5O_7$: C, 58.24; H, 6.45; N, 13.58. Found: C, 58.03; H, 6.41; N, 13.21.

(6) Z-Lys(Z)-Ser-Asp-Glu-Glu-Ser-OH (MW 874.857) (VI)

III (0.70 g, 1.0 mmole) was hydrogenated in methanol (50 ml) and 5% AcOH (10 ml) over Pd for 15 hr. After filtering and evaporating of the solvents, the residue was solidified by addition of ether. $Rf^I$ 0.15, $Rf^{II}$ 0.19. To a solution of Z-Lys(Z)-Ser-$N_2H_3$ (V) (0.62 g, 1.2 mmole) in N,N'-dimethylformamide (10 ml), 6N-HCl/dioxane (0.60 ml) was added with stirring at −15° C. To this mixture isoamylnitrite (0.16 ml) was added and then neutralized with triethylamine. The thus obtained azide solution was combined with a solution of the above obtained deprotected tetrapeptide in N,N'-dimethylformamide (5 ml) and $H_2O$ (5 ml) containing triethylamine (0.56 ml) with stirring at −15° C. The mixture was stirred at −15° C. for 2 hr. and at 4° C. for 15 hr. After removal of the solvent, the residue was solidified by addition of 1N citric acid and washed with $H_2O$. Reprecipitation was from methanol-ether acetate to yield (VI) (0.63 g, 72.0%). $Rf^I$ 0 53, $Rf^{II}$ 0.47 $[\alpha]_D^{24}$ −22.0 (C=1.03 methanol), (7) H-Lys-Ser-Asp-Glu-Glu-Ser-OH (MW 693.67) (VII)

(VI) (0.33 g, 0.38 mmole) was hydrogenated in methanol (30 ml) and 10% AcOH (10 ml) over Pd for 15 hr. After filtering and evaporating the solvent, the residue was solidified by addition of ethyl acetate (0.22 g, 83.5%). $Rf^I$ 0.04, $Rf^{II}$ 0.15, mp=175° C. $[\alpha]_D^{22}$=−31.2° C. (C=1.13 in $CH_3COOH$)

HPLC: $R_T$=5.5 minutes. (Solvent: 0.1M HCl: methanol, (98:2)).

Having now fully described the invention, it will be apparent to one of ordinary skill in the art that many changes and modifications can be made thereto without departing from the spirit of the invention as set forth herein.

What is claimed as new and desired to be secured by Letters Patent of the United States is:

1. a polypeptide consisting essentially of an amino acid sequence which is at least one member selected from the group consisting of:
(a) Ser-Glu-His-Glu-Thr-Arg,
(b) Gly-Ile-Lys-Ile-Arg,
(c) Arg-Leu-Pro-Ser-Asp-Asp,
(d) Asn-Asn-Ala-Asp-Gly-Asp,
(e) Glu-Ser-Asp-Arg-Pro-Asp,
(f) Lys-Asp-Tyr-Arg-Gly,
(g) Thr-Asp-Ser-Gly-Glu-Lys,
(h) Lys-Arg-Ala-Ser-Lys-Glu-Lys-Gln-Glu-Asn-Lys,
(i) Lys-Asn-Pro-Asp-Val-Lys,
(j) Lys-Ser-Asp-Glu-Glu-Ser,
(k) Asp-Tyr-Gly-Gly-Ile-Lys,
(l) Asp-Thr-Pro-Tyr-Leu-Asp,
(m) Arg-Ser-Pro-Ser-Thr-His; and
(n) at least one member selected from a pharmaceutically-acceptable acid-addition salt of amino acid sequences (a) to (m).

2. The polypeptide of claim 1 wherein said amino acid sequence is Ser-Glu-His-Glu-Thr-Arg, or a pharmaceutically-acceptable acid-addition salt thereof.

3. The polypeptide of claim 1 wherein said amino acid sequence is Gly-Ile-Lys-Lys-Ile-Arg, or a pharmaceutically-acceptable acid-addition salt thereof.

4. The polypeptide of claim 1 wherein said amino acid sequence is Arg-Leu-Pro-Ser-Asp-Asp, or a pharmaceutically-acceptable acid-addition salt thereof.

5. The polypeptide of claim 1 wherein said amino acid sequence is Asn-Asn-Ala-Gly-Asp, or a pharmaceutically-acceptable acid-addition salt thereof.

6. The polypeptide of claim 1 wherein said amino acid sequence is Glu-Ser-Asp-Arg-Pro-Asp, or a pharmaceutically-acceptable acid-addition salt thereof.

7. The polypeptide of claim 1 wherein said amino acid sequence is Lys-Asp-Tyr-Arg-Gly, or a pharmaceutically-acceptable acid-addition salt thereof.

8. The polypeptide of claim 1 wherein said amino acid sequence is Thr-Asp-Ser-Gly-Glu-Lys, or a pharmaceutically-acceptable acid-addition salt thereof.

9. The polypeptide of claim 1 wherein said amino acid sequence is Lys-Arg-Ala-Ser-Lys-Glu-Lys-Gln-Glu-Asn-Lys, or a pharmaceutically-acceptable acid-addition salt thereof.

10. The polypeptide of claim 1 wherein said amino acid sequence is Lys-Asn-Pro-Asp-Val-Lys, or a pharmaceutically-acceptable acid-addition salt thereof.

11. The polypeptide of claim 1 wherein said amino acid sequence is Lys-Ser-Asp-Glu-Glu-Ser, or a pharmaceutically-acceptable acid-addition salt thereof.

12. The polypeptide of claim 1 wherein said amino acid sequence is Asp-Tyr-Gly-Gly-Ile-Lys, or a pharmaceutically-acceptable acid-addition salt thereof.

13. The polypeptide of claim 1 wherein said amino acid sequence is Asp-Thr-Pro-Tyr-Leu-Asp, or a pharmaceutically-acceptable acid-addition salt thereof.

14. The polypeptide of claim 1 wherein said amino acid sequence is Arg-Ser-Pro-Ser-Thr-His, or a pharmaceutically-acceptable acid-addition salt thereof.

15. The polypeptide of claim 1 which has bound to one of its termini human albumin, bovine albumin, collagen, hemocyanin, fibrinogen, human erythrocyte, polyglutamic acid, polylysine, a lower alkyl of $C_{1-10}$, a lower acyl of $C_{1-10}$, an amino group, a lower alkyl amino of $C_{1-10}$, a di-lower alkyl amino of $C_{1-10}$ or a lower alkoxy of $C_{1-10}$.

* * * * *